United States Patent [19]

Hahn et al.

[11] Patent Number: 4,512,929
[45] Date of Patent: Apr. 23, 1985

[54] 1-ALKYL-2-ISOCYANATOMETHYL-ISOCYANATOBENZENES AND/OR 1-ALKYL-4-ISOCYANATOMETHYL-ISOCYANATOBENZENES

[75] Inventors: Erwin Hahn, Heidelberg; Peter Neumann, Wiesloch, both of Fed. Rep. of Germany

[73] Assignee: BASF Aktiengesellschaft, Ludwigshafen, Fed. Rep. of Germany

[21] Appl. No.: 478,696

[22] Filed: Mar. 25, 1983

[30] Foreign Application Priority Data

Apr. 7, 1982 [DE] Fed. Rep. of Germany ....... 3212927

[51] Int. Cl.³ .......................................... C07C 119/048
[52] U.S. Cl. .............................................. 260/453 AR
[58] Field of Search ................................. 260/453 AR

[56] References Cited

U.S. PATENT DOCUMENTS 4,079,073 3/1978 Bacskai ......................... 260/453 AR

OTHER PUBLICATIONS

Siefken, Annalen der Chemie, vol. 562, p. 126, (1949).

*Primary Examiner*—Dolph H. Torrence
*Attorney, Agent, or Firm*—Joseph D. Michaels

[57] ABSTRACT

The invention describes new aromatic diisocyanates having the formulas:

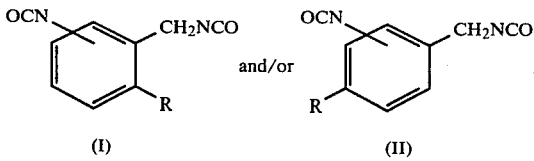

in which R is an alkyl radical with 1 to 12 carbon atoms. Preferably they are 1-alkyl-2-isocyanatomethyl-4-isocyanatobenzenes and/or 1-alkyl-4-isocyanatomethyl-2-isocyanatobenzenes and, particularly, 1-methyl-2-isocyanatomethyl-4- and -6-isocyanatobenzene and/or 1-methyl-4-isocyanatomethyl-2-isocyanatobenzene.

The new diisocyanates are preferably prepared by phosgenation of the corresponding diamines and subsequent thermal cleavage of the carbamic acid chlorides formed on an intermediary basis and are used for the preparation of plastics, preferably of polyurethanes, and crop protection agents.

9 Claims, No Drawings

1-ALKYL-2-ISOCYANATOMETHYL-ISOCYANATOBENZENES AND/OR 1-ALKYL-4-ISOCYANATOMETHYL-ISOCYANATOBENZENES

BACKGROUND OF THE INVENTION

1. Field of the Invention

The invention relates to the field of aromatic and aliphatic isocyanates in which two isocyanate groups of markedly different reactivity are present.

2. Description of the Prior Art

Aromatic diisocyanates such as 2,4- and 2,6-toluene diisocyanate, 1,5-naphthalene diisocyanate, 4,4'-diphenylmethane diisocyanate and mixtures of 4,4'-, 2,4'- and 2,2'-diphenylmethane diisocyanates and polyphenyl polymethylene polyisocyanates, aliphatic diisocyanates such as hexamethylene diisocyanate-1,6 and cycloaliphatic diisocyanates such as 3-isocyanatomethyl-3,3,5-trimethylcyclohexylisocyanate, are known commercial products which are preferably used in the preparation of polyurethane plastics. The polyisocyanates are commonly prepared from the corresponding amino compounds by phosgenation and subsequent thermal cleaving of the intermediate carbamic acid chlorides. Numerous organic mono- and polyisocyanates are described, for example, in the Annalen der Chemie 562 (1949), page 55, et seq.

SUMMARY OF THE INVENTION

The subject of the invention is an aromatic diisocyanate having a formula selected from the group consisting of

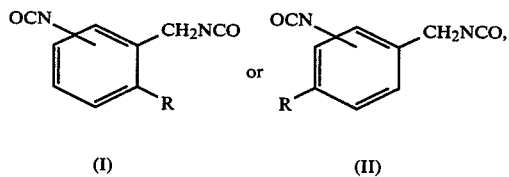

(I)  (II)

wherein R is an alkyl group with 1 to 12 carbon atoms and preferably where, in addition, the isocyanate group attached to the ring is in a position ortho or para to the alkyl group as shown in the following formulae:

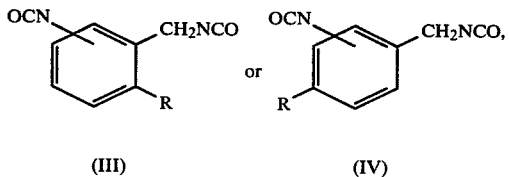

(III)  (IV)

The diisocyanates according to this invention have the desirable property of possessing two substituent isocyanate groups having different reactivities.

DESCRIPTION OF THE PREFERRED EMBODIMENTS

In the aforementioned formulae, the alkyl group, R, which consists of 1 to 12 carbon atoms, preferably 1 to 4 carbon atoms, may be linear or branched. Examples include alkyl radicals such as the n-pentyl, n-hexyl, n-heptyl, n-octyl, 2-ethyl-n-octyl, n-nonyl, n-decyl, n-undecyl, n-dodecyl radical, preferably the ethyl, n- and iso-propyl and n- and secondary butyl radical and particularly the methyl radical.

Detailed examples for the aromatic diisocyanates according to this invention include: 1-methyl-2-isocyanatomethyl-3-isocyanatobenzene, 1-methyl-2-isocyanatomethyl-5-isocyanatobenzene, 1-methyl-2-isocyanatomethyl-6-isocyanatobenzene, 1-methyl-4-isocyanatomethyl-3-isocyanatobenzene, 1-ethyl-2-isocyanatomethyl-3-isocyanatobenzene, 1-ethyl-2-isocyanatomethyl-5-isocyanatobenzene, 1-ethyl-2-isocyanatomethyl-6-isocyanatobenzene, 1-ethyl-4-isocyanatomethyl-3-isocyanatobenzene, 1-n-propyl-2-isocyanatomethyl-3-isocyanatobenzene, 1-n-propyl-2-isocyanatomethyl-5-isocyanatobenzene, 1-n-propyl-2-isocyanatomethyl-6-isocyanatobenzene, 1-n-propyl-4-isocyanatomethyl-3-isocyanatobenzene, 1-isopropyl-2-isocyanatomethyl-3-isocyanatobenzene, 1-iso-propyl-2-isocyanatomethyl-4-isocyanatobenzene, 1-iso-propyl-2-isocyanatomethyl-5-isocyanatobenzene, 1-iso-propyl-2-isocyanatomethyl-6-isocyanatobenzene, 1-iso-propyl-4-isocyanatomethyl-2-isocyanatobenzene, 1-iso-propyl-4-isocyanatomethyl-3-isocyanatobenzene, 1-n-butyl-2-isocyanatomethyl-3-isocyanatobenzene, 1-n-butyl-2-isocyanatomethyl-4-isocyanatobenzene, 1-n-butyl-2-isocyanatomethyl-5-isocyanatobenzene, 1-n-butyl-2-isocyanatomethyl-6-isocyanatobenzene, 1-n-butyl-4-isocyanatomethyl-2-isocyanatobenzene, 1-n-butyl-4-isocyanatomethyl-3-isocyanatobenzene, 1-n-pentyl-2-isocyanatomethyl-4-isocyanatobenzene, 1-n-pentyl-2-isocyanatomethyl-6-isocyanatobenzene, 1-n-pentyl-4-isocyanatomethyl-2-isocyanatobenzene, 1-n-hexyl-2-isocyanatomethyl-4-isocyanatobenzene, 1-n-hexyl-2-isocyanatomethyl-6-isocyanatobenzene, 1-n-hexyl-4-isocyanatomethyl-2-isocyanatobenzene, 1-n-heptyl-2-isocyanatomethyl-4-isocyanatobenzene, 1-n-heptyl-2-isocyanatomethyl-6-isocyanatobenzene, 1-n-heptyl-4-isocyanatomethyl-2-isocyanatobenzene, 1-n-octyl-2-isocyanatomethyl-4-isocyanatobenzene, 1-n-octyl-2-isocyanatomethyl-6-isocyanatobenzene, 1-n-octyl-4-isocyanatomethyl-2-isocyanatobenzene, 1-n-nonyl-2-isocyanatomethyl-4-isocyanatobenzene, 1-n-nonyl-2-isocyanatomethyl-6-isocyanatobenzene, 1-n-nonyl-4-isocyanatomethyl-2-isocyanatobenzene, 1-n-decyl-2-isocyanatomethyl-4-isocyanatobenzene, 1-n-decyl-2-isocyanatomethyl-6-isocyanatobenzene, 1-n-decyl-4-isocyanatomethyl-2-isocyanatobenzene, 1-n-undecyl-2-isocyanatomethyl-4-isocyanatobenzene, 1-n-undecyl-2-isocyanatomethyl-6-isocyanatobenzene, 1-n-undecyl-4-isocyanatomethyl-2-isocyanatobenzene, 1-n-dodecyl-2-isocyanatomethyl-4-isocyanatobenzene, 1-n-dodecyl-2-isocyanatomethyl-6-isocyanatobenzene, and 1-n-dodecyl-4-isocyanatomethyl-2-isocyanatobenzene. Preferably used are: 1-ethyl-2-isocyanatomethyl-4-isocyanatobenzene, 1-ethyl-4-isocyanatomethyl-2-isocyanatobenzene, 1-n-propyl-2-isocyanatomethyl-4-isocyanatobenzene and 1-n-propyl-4-isocyanatomethyl-2-isocyanatobenzene as well as particularly 1-methyl-2-isocyanatomethyl-4-isocyanatobenzene, 1-methyl-2-isocyanatomethyl-6-isocyanatobenzene as well as their isomer mixtures and 1-methyl-4-isocyanatomethyl-2-isocyanatobenzene.

The aromatic diisocyanates according to this invention may be used in the form of ring position isomer mixtures, mixtures of compounds with the same ring substitution but different alkyl radicals, or as mixtures of both mixtures.

The diisocyanates may be prepared, for example, according to the following process schematic:

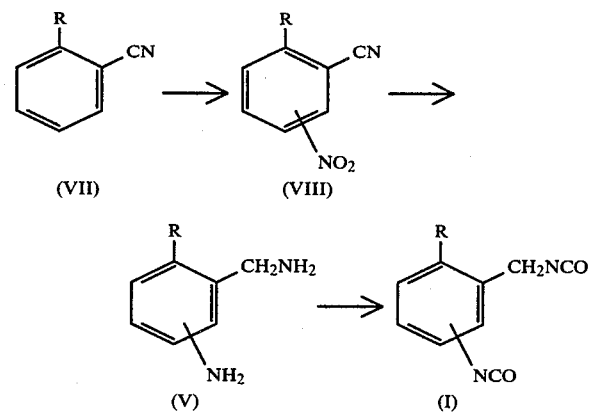

The 1-alkyl-2-cyanonitrobenzene (VIII) and/or the 1-alkyl-4-cyanonitrobenzenes may be prepared according to basically known methods by nitrating the corresponding 1-alkyl-2-cyano-benzenes (VII) or 1-alkyl-4-cyano-benzenes. These methods or suitable variations thereof are described, for example, in Berichte der Deutschen Chemischen Gesellschaft, vol. 31, pages 2880 and the following, (1898), or in the *Journal of the American Chemical Society*, vol. 99, page 6721, (1977). While nitration occurs predominantly in a position meta to the cyano group, some substitution occurs in all available positions on the ring.

Another example for a suitable method for the preparation of alkyl-cyano-nitrobenzene is the known exchange of the amino group of alkyl-amino-nitrobenzenes for a nitrile group corresponding with the *Journal of Organic Chemistry*, vol. 44, page 4003, (1979).

The 1-alkyl-cyano-nitrobenzenes produced by the nitration or their isomer mixtures may be reduced to 1-alkyl-aminomethyl-aminobenzenes or their isomer mixtures directly, that is, without further purification, for example, analogous with the method described in Farmaco (Pavia), Ediz. Sci. 25, 163 (1970)(C.A. 72, 121 101 d, 1970) for 2-cyano-nitrotoluene. The reduction of the nitro and the cyano group can be implemented in one or in two sequential reaction steps. The addition of ammonium is not always necessary.

The resultant 1-alkyl-aminomethyl-aminobenzenes can be phosgenated in solvents directly or as salts, preferably as hydrochlorides. Suitable solvents include toluene, xylene, chlorobenzene or dichlorobenzene. A solution of the 1-alkylaminomethyl-aminobenzenes or a suspension of the corresponding salts is then reacted with 1 to 3 moles, preferably 1.1 to 1.5 moles, of phosgene per NH2— or NH2.HCl groups at temperatures of approximately 0° C. to 100° C., preferably 10° C. to 50° C., and the carbamic acid chloride which is formed as an intermediate is cleaved into the 1-alkyl-isocyanatomethyl-isocyanatobenzene at temperatures of 80° C. to 180° C., preferably 120° C. to 160° C. The gaseous or liquid phosgene is added to the reaction mixture at such a rate that the escaping gases consist predominantly of hydrogen chloride.

After completion of the phosgenation and dehydrochlorination, the solvent is removed by distillation, preferably under reduced pressure, for example, 100 to 10 mbar. Optionally, it may also be advantageous to drive the hydrogen chloride and residual phosgene from the diisocyanate solution with the aid of nitrogen or another inert gas before the solvent is removed by distillation.

The resultant crude 1-alkyl-2- and/or -4-isocyanatomethyl-isocyanatobenzenes or isomer mixtures may be separated and purified by distillation under reduced pressure.

The aromatic diisocyanates according to this invention may also be produced by thermal cleavage of the corresponding diurethanes in the gas or liquid phase, possibly in the presence of catalysts whereby the diurethanes are advantageously prepared according to the method described in European published application No. 18 583 (U.S. Pat. No. 4,278,805) by reacting carbamate with the 1-alkyl-aminomethyl-aminobenzenes in the presence of alcohols and possibly urea.

The 1-alkyl-2- or -4-isocyanatomethyl-isocyanatobenzenes are valuable raw materials for crop protection agents and plastics. The products are particularly well suited for the preparation of polyurethanes foams, polyurethane adhesives, lacquers and coating agents and polyurethane sealants.

The following examples are intended to describe the preparation of the invention in greater detail without, however, being limiting.

EXAMPLE 1

(a) Preparation of an isomer mixture of 1-methyl-2-isocyano-4-nitrobenzene and 1-methyl-2-isocyano-6-nitrobenzene In a reaction vessel equipped with drip funnel, agitator and thermometer, 1200 parts by weight of concentrated sulfuric acid were cooled to −5° C. While stirring the mixture well, 200 parts by weight of 2-cyano-toluene were added within one hour followed by 151 parts by weight of concentrated nitric acid added slowly at a temperature between −5° C. and +5° C. throughout the addition. To complete the nitration, the mixture was stirred for another 1.5 hours at 0° C., and the reaction mixture was then poured onto 2000 parts by weight of ice. The precipitate was recovered by filtration, thoroughly washed with water and dried on clay. The result was 282 parts by weight of a crude isomer mixture of 1-methyl-2-cyano-4- and -6-nitrobenzene in a weight ratio of approximately 87:13 having a melting point of 91° to 92° C.

(b) Preparation of an isomer mixture of 1-methyl-2-aminomethyl-4- and -6-aminobenzene One hundred parts by weight of the 1-methyl-2-cyano-4- and -6-nitrobenzene isomer mixture obtained in accordance with (a) were dissolved in 800 parts by weight of ethanol and were hydrogenated at 50 bar and 80° C. after adding 25 parts by weight of Raney nickel. After cooling to room temperature, the catalyst was removed by filtration, and the filtrate was concentrated under reduced pressure. The result was 80 parts by weight of a crude mixture of 1-methyl-2-aminomethyl-4- and -6-aminobenzene in form of an oil which quickly solidified.

$C_8H_{12}N_2$ (molecular weight 136, mass spectrometrically).

(c) Preparation of an isomer mixture of 1-methyl-2-isocyanatomethyl-4- and -6-isocyanatobenzene With stirring, a solution of 27.2 parts by weight of the isomer mixture of 1-methyl-2-aminomethyl-4- and -6-aminobenzene, maintained at 50° to 60° C. in 200 parts by weight of o-dichlorobenzene, were added dropwise to a mixture of 520 parts by weight of o-dichlorobenzene and 160 parts by weight of phosgene which had been cooled to 0° C. After completing the addition, the mixture was slowly heated to 130° C. and, at this temperature, phosgene was directed through the reaction mixture for a period of 1.5 hours. Subsequently, the reaction mixture was allowed to cool to room temperature and the excess phosgene was removed by blowing with a jet of nitrogen. Following this process, the solvent was initially removed by distillation at 10 to 20 mbars and the residue was thereafter distilled under a high vacuum (0.05 mbar). The result was 19.2 parts by weight of a mixture of 1-methyl-2-isocyanatomethyl-4- and -6-isocyanatobenzene in a weight ratio of 87:13 with a boiling point of 100° to 105° C. (0.05 mbar).

| Analysis: $C_{10}H_8N_2O_2$ (molecular weight: 188, mass spectrometrically) | | | | |
|---|---|---|---|---|
| | C | H | O | N |
| Calculated: | 63.83 | 4.28 | 14.89 | 17.00 |
| Determined: | 63.7 | 4.4 | 14.8 | 16.6 |

EXAMPLE 2

(a) Preparation of 1-methyl-4-cyano-2-nitrobenzene

An amount of 240 parts by weight of concentrated sulfuric acid was cooled to −5° C. in a reaction vessel equipped with a drip funnel, agitator and thermometer. While stirring the mixture well, 40 parts by weight of 4-cyanotoluene were added portionwise and 25 volume parts of concentrated nitric acid were then added dropwise at a temperature between −5° C. and +5° C. To complete the nitration, the mixture was agitated at 0° C. for two hours and the reaction mixture was then poured onto 400 parts by weight of ice. The precipitate was recovered by filtration, thoroughly washed with water and dried in air. The result was 50.9 parts by weight of 1-methyl-4-cyano-2-nitrobenzene with a melting point of 105° to 106° C.

(b) Preparation of 1-methyl-4-aminomethyl-2-aminobenzene

Fifty parts by weight of the 1-methyl-4-cyano-2-nitrobenzene produced in accordance with (a) were dissolved in 500 parts by weight of ethanol. Fifteen parts by weight of Raney nickel were added and the cyanonitro compound hydrogenated at 10 bars and 60° C. until the hydrogen absorption was completed. After adding 5 volume parts of 3 percent ammonium solution the mixture was again hydrogenated at 10 bars and 60° C. After cooling to room temperature, the catalyst was removed by filtration and the filtrate was concentrated under reduced pressure. The result was 37.9 parts by weight of crude 1-methyl-4-aminomethyl-2-aminobenzene in form of an oil which crystalized on standing.

(c) Preparation of 1-methyl-4-isocyanatomethyl-2-isocyanatobenzene

While stirring, a solution of 13.6 parts by weight of the 1-methyl-4-aminomethyl-2-aminobenzene obtained according to (b) in 100 parts by weight of o-dichlorobenzene were added dropwise to a mixture of 260 parts by weight of o-dichlorobenzene and 80 parts by weight of phosgene cooled to 0° C. After completing addition, the mixture was slowly heated to 160° C. and phosgene was directed through this reaction mixture at this temperature for two hours. Subsequently, the reaction mixture was allowed to cool to room temperature and the excess phosgene was separated by introducing nitrogen. Following this process, the solvent was removed by distillation at 10 to 20 mbar and the residue was thereafter distilled under a high vacuum (0.05 mbar). The result was 9.6 parts by weight of 1-methyl-4-isocyanatomethyl-2-isocyanatobenzene with a boiling point of 103° to 105° C. (0.05 mbar).

The embodiments of the invention in which an exclusive property or privilege is claimed are defined as follows:

1. An aromatic diisocyanate having a formula selected from the group consisting of

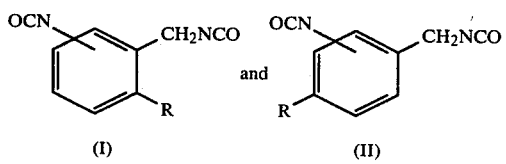

in which R is an alkyl group with 1 to 12 carbon atoms.

2. An aromatic diisocyanate having a formula selected from the group consisting of

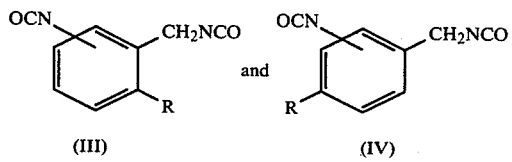

in which R is an alkyl group with 1 to 12 carbon atoms.

3. A mixture of aromatic diisocyanates selected from those of claim 1.

4. A mixture of aromatic diisocyanates selected from those of claim 2.

5. The aromatic diisocyanates of claim 2 wherein R is selected from the group consisting of methyl, ethyl, n-propyl, isopropyl, n-butyl, and sec-butyl.

6. The aromatic diisocyanate of formula (I), claim 1, wherein R is a methyl group and the ring isocyanate group is attached para to the methyl group.

7. The aromatic diisocyanate of formula (I), claim 1, wherein R is a methyl group and the ring isocyanate group is attached ortho to the methyl group.

8. The aromatic diisocyanate of formula (II), claim 1, wherein R is a methyl group and the ring isocyanate group is attached ortho to the methyl group.

9. An isomer mixture of the aromatic diisocyanates of formula (I) in claim 1 wherein R is a methyl group and the ring-attached isocyanate group is ortho to the methyl in one isomer and para to the methyl in the second isomer in a ratio of approximately 10 to 15 parts of ortho isomer to 80 to 85 parts para isomer.

* * * * *